(12) United States Patent
Rutten et al.

(10) Patent No.: US 9,327,133 B2
(45) Date of Patent: May 3, 2016

(54) IMPLANTABLE MEDICAL DEVICE

(75) Inventors: Jean J. G. Rutten, Bocholtz (NL); Karel F. A. A. Smits, Munstergeleen (NL)

(73) Assignee: Medtronic, Inc., Minneapolis, MN (US)

( * ) Notice: Subject to any disclaimer, the term of this patent is extended or adjusted under 35 U.S.C. 154(b) by 2145 days.

(21) Appl. No.: 11/379,287

(22) Filed: Apr. 19, 2006

(65) Prior Publication Data

US 2007/0250123 A1 Oct. 25, 2007

(51) Int. Cl.
*A61N 1/375* (2006.01)

(52) U.S. Cl.
CPC .............. *A61N 1/375* (2013.01); *A61N 1/3752* (2013.01)

(58) Field of Classification Search
CPC .............................. A61N 1/056; A61N 1/3752
USPC .............................................. 607/2, 4, 5, 128
See application file for complete search history.

(56) References Cited

U.S. PATENT DOCUMENTS

| 4,013,081 | A | * | 3/1977 | Kolenik .......................... 607/9 |
| 5,076,272 | A | | 12/1991 | Ferek-Petric |
| 5,313,953 | A | | 5/1994 | Yomtov et al. |
| 5,331,966 | A | | 7/1994 | Bennett et al. |
| 5,439,484 | A | | 8/1995 | Mehra |
| 6,522,915 | B1 | | 2/2003 | Ceballos et al. |
| 6,647,292 | B1 | | 11/2003 | Bardy et al. |
| 6,721,597 | B1 | | 4/2004 | Bardy et al. |
| 6,950,705 | B2 | | 9/2005 | Bardy et al. |
| 2004/0093039 | A1 | | 5/2004 | Schumert |
| 2005/0192507 | A1 | * | 9/2005 | Warren et al. ................. 600/512 |
| 2006/0030893 | A1 | | 2/2006 | Laske et al. |
| 2007/0038280 | A1 | * | 2/2007 | Bodner et al. ................ 607/128 |

* cited by examiner

*Primary Examiner* — Christopher D. Koharski
*Assistant Examiner* — Michael D Abreu (57) ABSTRACT

An implantable medical device is provided for sensing cardiac activity within a patient's body. The device comprises a canister, control circuitry disposed within the canister, and a lead assembly extending from the canister. At least one sense electrode is coupled to the circuitry and disposed on the lead assembly for sensing cardiac activity. At least one spacer is coupled between the lead assembly and the canister for maintaining a minimum predetermined distance between the at least one sense electrode and the canister.

20 Claims, 5 Drawing Sheets

IMPLANTABLE MEDICAL DEVICE

TECHNICAL FIELD

This invention relates generally to an implantable medical device and, more particularly, to an implantable cardioverter defibrillator wherein the positioning of a plurality of sense electrodes is maintained with respect to each other and with respect to defibrillator's canister.

BACKGROUND OF THE INVENTION

Cardiac muscle is rhythmyogenic; i.e., without any external electrical stimulus, the muscle cells of the heart will spontaneously self-excite and contract. However, without some form of pacing, the heart will enter into a state of fibrillation wherein the cardiac muscle cells contract rapidly in an irregular and unsynchronized manner. Fortunately, specialized pacemaker cells coordinate the beating of the heart. These pacemaker cells are collected at two nodes, the sinoatrial node and the atrioventricular node. The sinoatrial node spontaneously initiates a heartbeat by electrically stimulating muscle cells within the upper right atrium, which causes the right and left atrium to contract as the electrical impulses propagate through the surrounding cardiac tissue. When the electrical impulses reach the lower portion of the right atrium, the atrioventricular node then causes the ventricles to contract thereby completing a heartbeat.

A heart may beat incorrectly in several ways. That is, it may beat too quickly (tachycardia), too slowly (bradycardia), or the upper or lower chambers of the heart may contract in an unsynchronized, erratic manner (fibrillation). Each of these arrhythmias typically requires treatment; however, ventricular fibrillation requires immediate medical attention. To treat an arrhythmia, external electrical stimulation may be applied to the heart. Tachycardia, bradycardia, and atrial fibrillation may be addressed through cardioversion, which uses low level electrical pulses (or drug therapy) to return a heart to its normal rhythm. In contrast, ventricular fibrillation is treated with defibrillation wherein a more aggressive therapy is applied to the heart.

Implantable cardioverter defibrillator (ICDS) have been developed that may deliver low level electrical pulses to help pace a patient's heart and, if necessary, deliver high level electrical pulses to treat ventricular fibrillation. In general, an ICD comprises a pulse generator and a flexible lead assembly having a distal end and a proximal end coupled to the pulse generator. One or more pacing electrodes and one or more coiled defibrillation electrodes are disposed on the distal end of the lead assembly. When the pulse generator is implanted within a patient, the lead assembly is disposed proximate the patient's heart. If a transvenous ICD is employed, the distal end of the lead assembly is positioned within one or more chambers of the heart (endocardial lead), on the surface of the heart (epicardial lead), or within the surrounding vasculature. If a subcutaneous ICD is employed, the distal end of the lead assembly is positioned adjacent the heart.

An ICD should be capable of identifying and distinguishing between the different types of arrhythmias to determine the proper treatment to apply. To this end, ICDs may be equipped with one or more sense electrodes proximally disposed on the flexible lead assembly. Each of the sense electrodes register cardiac (or other bioelectric) signals and transmit these signals to control circuitry disposed within the ICD, which then determines if a particular arrhythmia has been detected. Since the sense electrodes are deployed on a flexible lead assembly, the position of the electrodes may move with respect to each and with respect to the pulse generator's conductive canister. This introduces a level of uncertainty in the detection of the cardiac signals. For example, the conductive canister may affect (e.g., attenuate) the bioelectric signals at the sense electrodes, which, in turn, makes accurate identification of arrhythmic conditions more difficult. If the sense electrodes are physically contacting the conductive canister, further interference with signal detection is possible.

Considering the above, it should be appreciated that it would be desirable to provide an implantable medical device (e.g., an ICD) wherein the relative positioning of the sense electrodes is maintained, and may be duplicated if desired. It would also be desirable to provide such a subcutaneous implantable cardiac sensing and/or treatment device wherein the sensing electrodes are maintained at least a predetermined distance from the system's conductive canister. Furthermore, other desirable features and characteristics of the present invention will become apparent from the subsequent detailed description of the invention and the appended claims, taken in conjunction with the accompanying drawings and this background of the invention.

BRIEF DESCRIPTION OF THE DRAWINGS

The following drawings are illustrative of particular embodiments of the invention and therefore do not limit the scope of the invention, but are presented to assist in providing a proper understanding. The drawings are not to scale (unless so stated) and are intended for use in conjunction with the explanations in the following detailed descriptions. The present invention will hereinafter be described in conjunction with the appended drawings, wherein like reference numerals denote like elements, and.

DETAILED DESCRIPTION OF THE EXEMPLARY EMBODIMENT

The following description is exemplary in nature and is not intended to limit the scope, applicability, or configuration of the invention in any way. Rather, the following description provides a convenient illustration for implementing an exemplary embodiment of the invention. Various changes to the described embodiment may be made in the function and arrangement of the elements described herein without departing from the scope of the invention.

Figure 1:
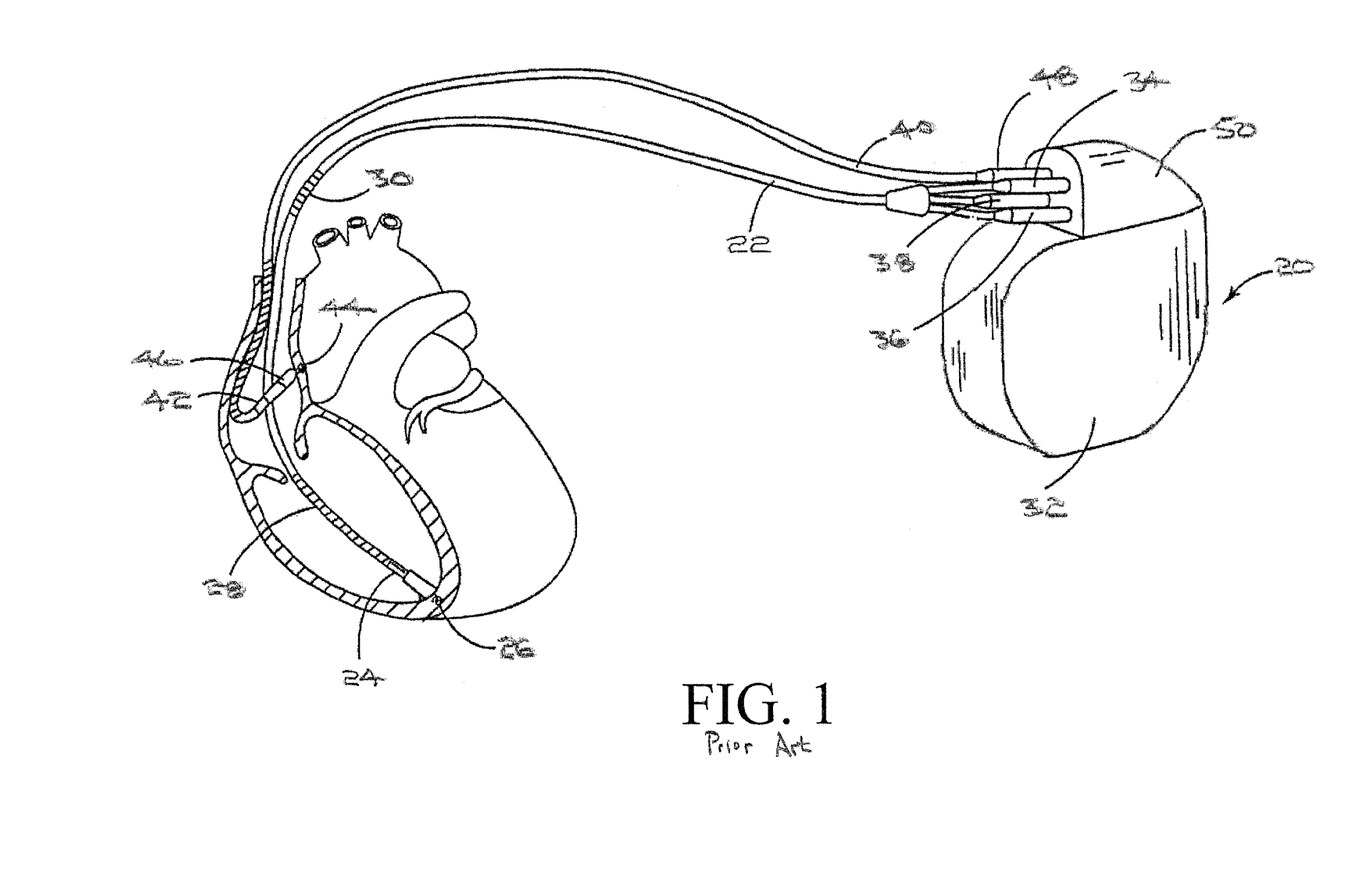
FIG. 1 is an isometric view of an implanted transvenous ICD in accordance with the prior art.

FIG. 1 is an isometric view of a transvenous ICD system 20. In a subcutaneously placed ICD, cardiac activity can be sensed and therapy delivered by means of an electrode system that does not require insertion of an electrode into a heart chamber, a heart muscle, or the patient's vasculature. The heart is monitored using a canister coupled to a lead assembly. The canister may have an electrode thereon, and the lead assembly includes several sense electrodes. A coil electrode may act as a therapy delivery electrode as well as a sense electrode.

In the lead assembly shown in FIG. 1, a ventricular lead includes an elongated insulative lead body 22 carrying four insulated conductors. A ring electrode 24, an extendable helix electrode 26, and elongated coil electrodes 28 and 30 are associated with lead body 22. Electrodes 24 and 26 are employed for cardiac pacing and for sensing ventricular depolarization, and electrodes 28 and 30 are used in conjunction with housing 32 for delivering ventricular cardioversion and defibrillation pulses. Two unipolar connectors 34 and 36 are coupled to coil electrodes 28 and 30. Electrical connector 38 is provided with a connector ring and a connector pin that are electrically coupled to electrodes 24 and 26, respectively.

The atrial lead includes an elongated insulative body carrying two insulated concentric-coiled conductors. Located adjacent the distal end are a ring electrode 42 and an extendable helix electrode 44 mounted retractably within an insulative electrode head 46. Electrodes 44 and 42 are used for atrial pacing and for sensing atrial depolarizations. An inline connector 48 carries a connector ring and a connector pin, and is coupled to electrodes 42 and 44, respectively. The system also includes lead connectors 34, 36, 38, and 48 that are inserted into connector block 50, which, in turn, contains corresponding electrical connectors for coupling to the various connector rings and pins and to circuitry contained within canister 32.

Figure 2:
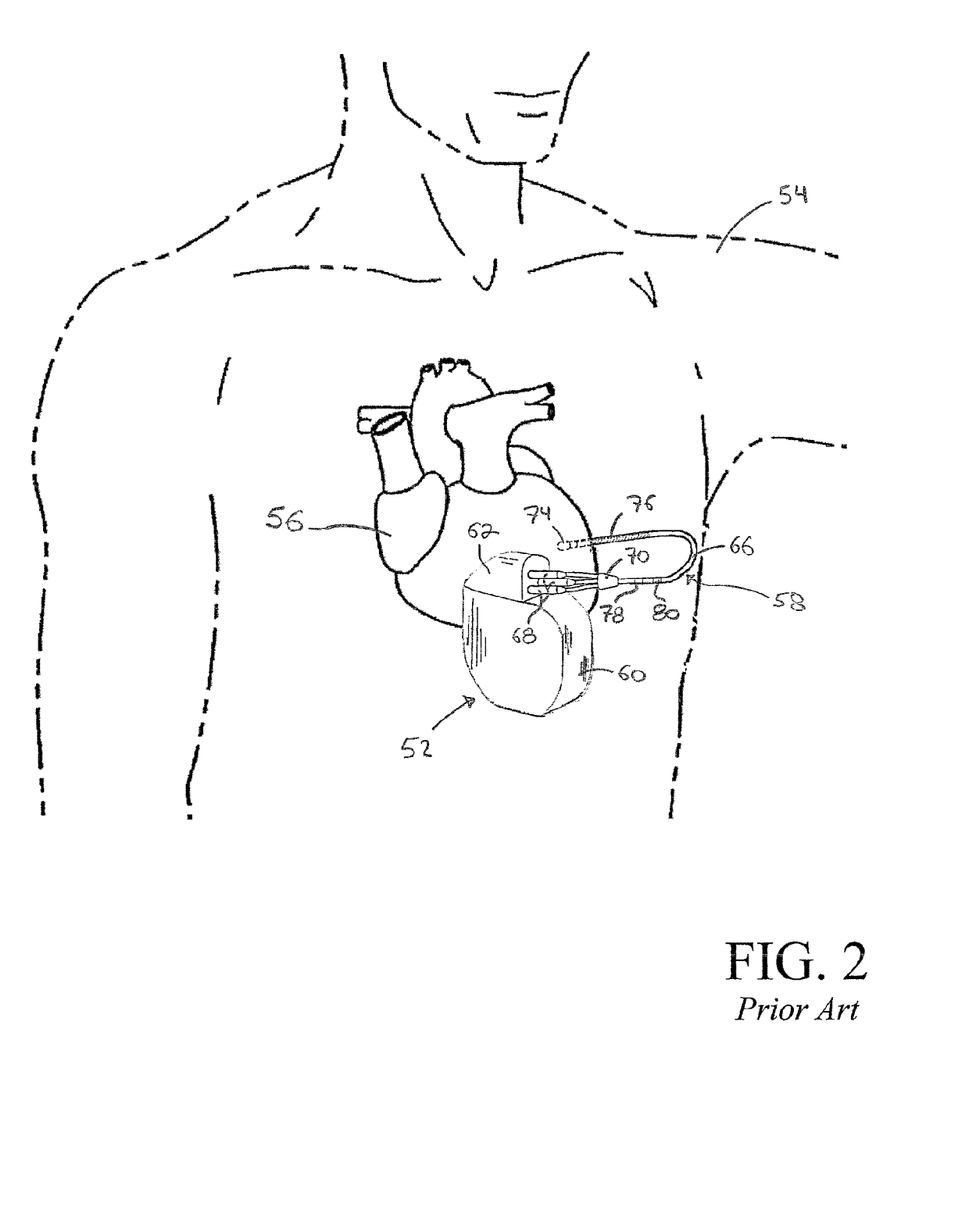
FIG. 2 is an isometric view of an implanted subcutaneous ICD in accordance with the prior art.

FIG. 2 is an isometric view of a known subcutaneous ICD 52 implanted in a patient 54 proximate heart 56. ICD 52 comprises an elongated subcutaneous lead assembly 58 and a pulse generator 60 including a connector block 62. ICD 52 is positioned within patient 54 such that heart 56 resides between ICD 52 and the distal end portion of lead assembly 58. Lead assembly 58 comprises a unitary lead body 66 and a plurality of lead legs 68, which are joined to lead body 64 via furcation (e.g., trifurcation) 70. Lead legs 68 are each coupled to pulse generator 60 through connector block 62. A plurality of electrodes is disposed on unitary lead body 66. These electrodes may include, for example, a tip electrode 74 and a coil electrode 76 disposed along a distal portion of unitary lead body 66, and two sense electrodes 78 and 80 disposed along a proximal portion of body 66 (e.g., substantially adjacent trifurcation 70). Electrodes 74, 76, 78, and 80 are each coupled to pulse generator 60 (or, more accurately, to control circuitry disposed within pulse generator 60) by way of one or more conductive filars contained within lead body 66 and lead legs 68.

Coil electrode 76 is utilized to deliver high level defibrillation therapy to heart 56 if heart 56 is experiencing ventricular fibrillation. ICD 52 determines if heart 56 is experiencing an arrhythmia by monitoring bioelectric signals indicative of cardiac activity via tip electrode 74 and sense electrodes 78 and 80. Precise sensing and identification of cardiac signals is necessary to enable ICD 52 to accurately identify and properly treat arrhythmic conditions occurring within heart 56. However, lead assembly 58 may not always achieve precise sensing due to the disposition of the proximal sense electrodes on lead body 66. That is, as a result of their disposal on flexible lead body 66, sense electrodes 78 and 80 are permitted to move relative to one another and relative to the conductive canister of pulse generator 60. Consequently, the conductive canister of pulse generator 60 may have an unpredictable effect on the signals received at sense electrodes 78 and 80, thereby making it more difficult for ICD 52 to accurately and rapidly identify arrhythmic conditions within heart 56.

Figure 3:
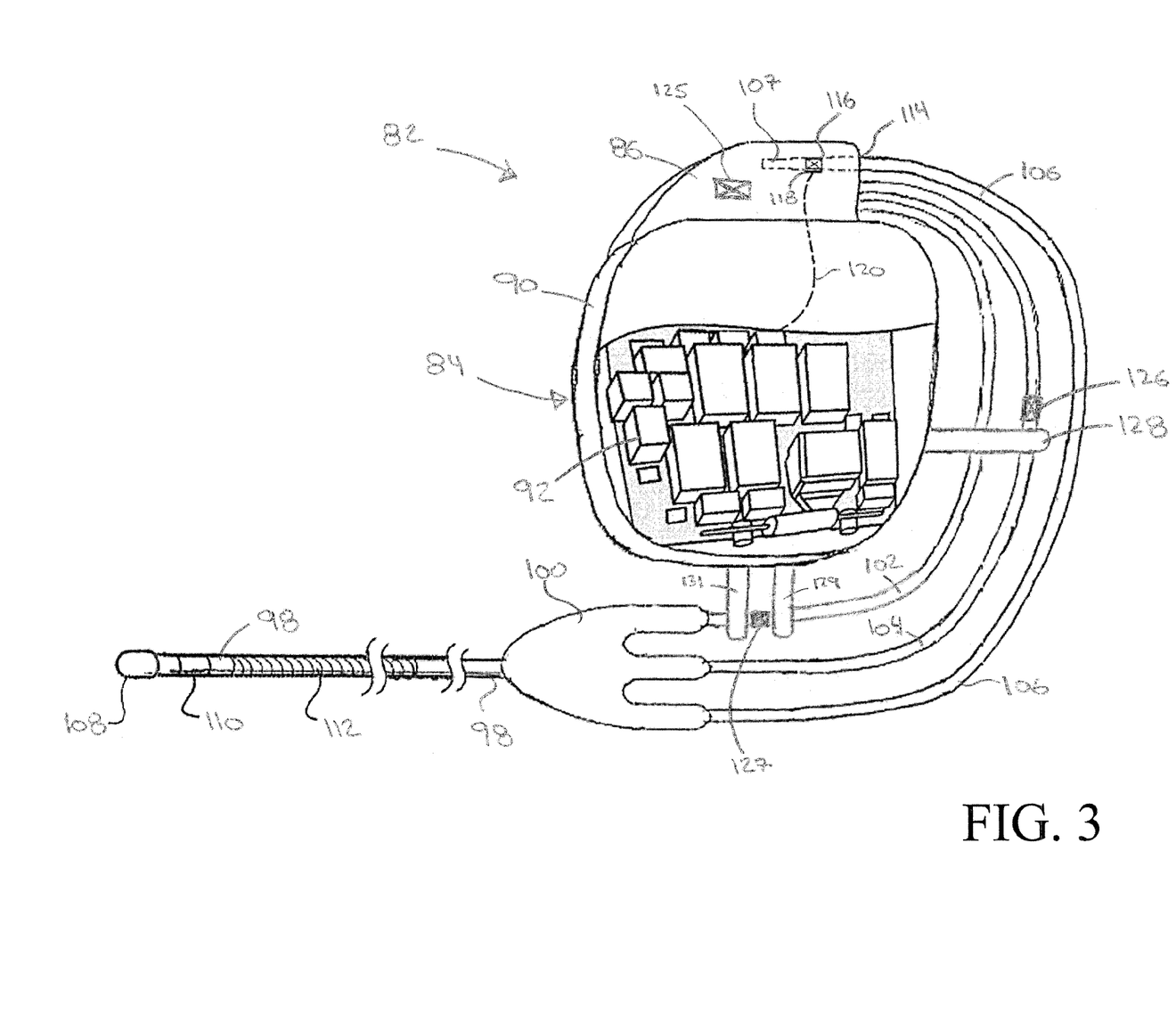
FIGS. 3 and 4 are isometric views of subcutaneous ICDs in accordance with a first and second embodiments, respectively, of the present invention.

FIG. 3 is an isometric cutaway view of an implantable cardioverter defibrillator 82 in accordance with a first embodiment of the present invention. ICD 82 is similar to ICD 52 described above in conjunction with FIG. 2; i.e., ICD 82 includes a pulse generator 84 comprising a conductive canister 90 (e.g., titanium, stainless steel, aluminum, etc.) having control circuitry 92 disposed therein. A connector block 86 is fixedly coupled to canister 90, and an elongated lead assembly 88 is coupled to block 86. Lead assembly 88 includes a unitary lead body 98, which extends from a distal portion to a proximal portion of assembly 88 to meet a trifurcation 100. Trifurcation 100 couples lead body 98 to three lead legs 102, 104, and 106, which are each received by connector block 86 in the manner described below. A plurality of electrodes is distally disposed on unitary lead body 98. If, for example, lead assembly 88 is a tripolar lead assembly, a tip electrode 108, a ring electrode 110, and a coil electrode 112 may be disposed along a distal end portion of lead body 98. In particular, tip electrode 108 may be disposed on the distal tip of lead body 98, ring electrode 110 may be positioned approximately 8 millimeters from electrode 108, and coil electrode 112 may be positioned approximately 12 millimeters from ring electrode 110. Coil electrode 112 may be straight and 150 to 250 millimeters in length, or electrode 112 may be sigmoidal, coiled, or U-shaped and approximately 250 to 600 millimeters in length. Coil electrode 112 may be utilized to deliver defibrillating pulses to a patient's heart as described in more detail below. As will be appreciated by one skilled in the art, electrodes 108 and 110 may also be utilized to deliver low level pacing pulses in endocardial (e.g., right ventricular) or epicardial lead applications.

Lead body 98 comprises an insulative tubing that guides a plurality of conductive filars, each of which is coupled to a different electrode distally disposed on lead body 98 (i.e., tip electrode 108, ring electrode 110, or coil electrode 112). For example, lead body 98 may comprise a polyurethane or silicon tube having an insulative silicon core. Each filar passes through the silicon core, possibly within a narrower polyurethane tube to provide redundant insulation. It should thus be appreciated that each electrode disposed on lead body 98, and each filar running within lead body 98, is electrically isolated.

As stated previously, the proximal end of lead body 98 is coupled to lead legs 102, 104, and 106 via trifurcation 100. Trifurcation 100 comprises an insulative body that directs each of the filars running within lead body 98 into a different one of lead legs 102, 104, and 106. For example, trifurcation 100 may direct the filars associated with tip electrode 108, ring electrode 110, and coil electrode 112 into lead legs 102, 104, and 106, respectively. Lead legs 102, 104, and 106 are each provided with a proximal connector end, preferably in the form of a standard IS-1 or DF1 connector, which may be plugged into one of three ports provided in connector block 86. Only proximal end 107 of lead leg 106 is shown in FIG. 2 for clarity. As can be seen, proximal end 107 of lead leg 106 is received within a port 114 provided in connector block 86. A setscrew block (not shown) is provided within connector block 86 and tightened (e.g., via a torque wrench) upon insertion of lead leg 106 to secure proximal end 107 within port 114. If desired, the proximal end 107 may be provided within one or more circumferential ribs to facilitate the connection.

A ring connector 116 is provided around proximal end 107 of lead leg 106, and similar ring connectors are provided around the proximal ends of legs 102 and 104. Ring connector 116 is electrically coupled to the filar running within lead leg 106 and, therefore, to coil electrode 112. When lead leg 106 is inserted into port 114, ring connector 116 engages an electrical contact 118 provided within connector block 86. Contact 118 is electrically coupled to control circuitry 92 by way of an electrical path 120 (e.g., a gold wire). Thus, by inserting proximal end 107 of lead leg 106 into port 114, coil electrode 112 is electrically coupled to control circuitry 92. Tip electrode 108 and ring electrode 110 are likewise coupled to control circuitry 92 via insertion of the proximal ends of lead legs 104 and 106, respectively, into connector block 86.

ICD 82 may be surgically positioned in a patient such the patient's heart is positioned between electrode 112 of assembly 88 and canister 90 of pulse generator 84. After implantation, ICD 82 will monitor cardiac activity to determine whether the patient's heart is experiencing an arrhythmia. To enable ICD 82 to better detect cardiac signals emitted by the heart, two sense electrodes 126 and 127 are provided along a proximal portion of electrode assembly 88. For example, sense electrodes 126 and 127 may be disposed on the same one or different ones of the lead legs. In the embodiment illustrated in FIG. 3, sense electrodes 126 and 127 are disposed on lead legs 104 and 102, respectively. Sense electrodes 126 and 127 are coupled to control circuitry 92 in substantially the same manner as are electrodes 108, 110, and 112.

ICD 130 may also include a third sense electrode 125 disposed on connector block 86. Sense electrode 125 is electrically isolated from the conductive canister of pulse generator 84. Sense electrode 125 is coupled to control circuitry disposed within pulse generator 84, and may provide at least two additional sensing vectors (i.e., from electrode 125 to electrode 126, and from electrode 125 to electrode 127) to control circuitry 92. Because electrode 125 resides within connector block 86, the spatial disposition of sense electrode 125 is fixed relative to canister 90.

The positioning of sense electrodes 126 and 127 is maintained by a plurality of spacers; e.g., first, second, and third spacers 128, 129, and 131. In the embodiment shown in FIG. 3, spacers 128, 129, and 131 each function as a separator; e.g., an insulative body (e.g., plastic, silicon, etc.) that extends outwardly from a lead leg (i.e., lead leg 104 in the case of spacer 128, and lead leg 102 in the case of spacers 129 and 131) to contact canister 90. To provide optimal support to the proximal sensing electrodes, separator 128 may be coupled to lead leg 104 proximate sense electrode 126 (e.g., lead leg 104 may pass through a channel provided through separator 128), and separators 129 and 131 may be coupled to lead leg 102 proximate opposite sides of sense electrode 127. Insulative separators 128, 129, and 131 thus serve to position electrodes 126 and 127 with respect to each other and with respect to pulse generator 84. Separators 128, 129, and 131 also prevent electrodes 126 and 127 from contacting conductive canister 90 and any other electrodes disposed on other lead legs.

Figure 4:
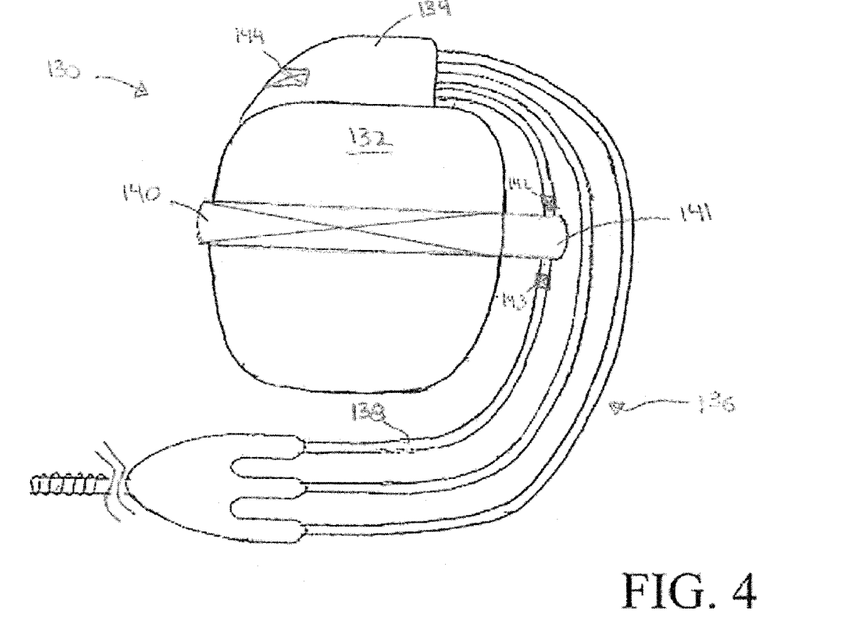

It is not required that separators 128, 129, and 131 are physically connected to pulse generator 84. Instead, separators 128, 129, and 131 may be configured to abut canister 90 when ICD 82 is implanted and lead assembly 88 is wrapped around an outer perimeter of pulse generator 84 as shown in FIGS. 3 and 4. If desired, the portion of insulative separators 128, 129, and 131 contacting canister 90 may be curved or U-shaped to better stabilize electrodes 126 and 127 with respect to pulse generator 84. By not fixedly coupling separators 128, 129, and 131 to generator 84, the modular nature of lead assembly 88 may be preserved (e.g., lead assembly 88 may still be freely interchanged with other lead assemblies).

Control circuitry 92 utilizes sense electrodes 126 and 127 in conjunction with tip electrode 108, sense electrode 125 in connector block 86, and ring electrode 110 to monitor cardiac activity. By utilizing multiple sense electrodes, control circuitry 92 may compare data gathered from a variety of sensing vectors to better identify the strength and direction of the bioelectric waves in three-dimensional space. If an arrhythmia is detected within the patient's heart, ICD 82 will determine the appropriate therapy to be applied. If ICD 82 determines that the electrical signals (in particular, the QRS complex) registered by the sense electrodes (i.e., electrodes 108, 110, 125, 126, and 127) is indicative of ventricular fibrillation, ICD 82 will act as a defibrillator and cause coil electrode 112 to deliver a high level transthoracic therapy across the patient's heart. If necessary, ICD 82 may also deliver high level emergency pacing between canister 90 and coil electrode 112. It should be appreciated that lead body may also be configured to be an epicardial or endocardial lead, in which case ICD 82 may utilize tip electrode 108 and/or ring electrode 110 to administer low level pacing therapy if control circuitry 92 determines that the heart is experiencing bradycardia, tachycardia, or atrial fibrillation.

FIG. 4 is an implantable cardioverter defibrillator 130 in accordance with a second embodiment of the present invention. As was the case with ICD 82 (FIG. 3), ICD 130 comprises a pulse generator 132, a connector block 134 fixedly coupled to generator 132, and an elongated lead assembly 136 coupled to block 134. Lead assembly 136 includes a first lead leg 138 having two sense electrodes 142 and 143 disposed thereon, which may monitor cardiac activity in the manner described above. A third sense electrode 144 may also be disposed on connector block 134 in the manner described above. In contrast to ICD 82, ICD 130 includes a shroud 140 there around (e.g., plastic, silicon, etc.) that functions as a spacer. Shroud 140 extends around a circumference of pulse generator 132, and includes an insulative extension or arm 141 that protrudes outwardly from pulse generator 132 to engage lead leg 138 proximate sense electrodes 142 and 143. Arm 141 may be coupled to lead leg 138 in a variety of ways. For example, arm 141 may include a channel therethrough through which lead leg 138 is threaded. Alternatively, arm 141 may include a slot therein into which lead leg 138 may be press-fit. Shroud 140 thus serves to maintain the spatial orientation of sense electrodes 142 and 143 relative to each other and to pulse generator 132.

Though ICD 82 and ICD 130 have been described as having some or all of the proximal sense electrodes (e.g., electrodes 126, 127, 142, and 143) disposed on a lead leg, one or more of the sense electrodes may be disposed elsewhere on the lead assembly. This point is further illustrated in FIG. 5, which is an isometric view of a lead assembly 150. Lead assembly 150 comprises a unitary lead body 152 and a plurality of lead legs 154 joined to lead body 152 by way of a trifurcation 156. In this embodiment, two sense electrodes 158 and 160 are disposed at selected positions on trifurcation 156. Sense electrodes 158 and 160 are thus spatially fixed relative to one another. When lead assembly 150 is employed with an implantable medical device (e.g., pulse generator 84 or 132), the position of trifurcation 156 is secured relative to that of the device's canister by one or more spacers (e.g., one or more separators, such as separators 128, 129, and 131 shown in FIG. 3; or a shroud, such as shroud 140 shown in FIG. 4). In this way, lead assembly 150 may maintain the relative position of sense electrodes 158 and 160 with respect to the device's conductive canister to facilitate the accurate detection of cardiac activity.

Figure 6:
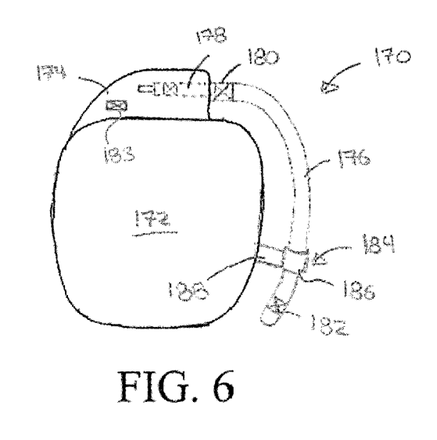
FIG. 6 is an isometric view of an implantable medical device having a flexible plug in accordance with a fourth embodiment of the present invention.

It should be understood that the inventive medical device need not be an ICD, but may instead be any one of a multitude of implantable medical devices (IMDs), such as an implantable cardio-monitor. FIG. 6 illustrates an IMD 170 comprising a canister 172, a connector block 174 fixedly coupled to canister 172, and a lead body or flexible plug 176 (e.g., silicon) coupled to connector block 174. Plug 176 includes a proximal tip 178 that is received within connector block 174 in a manner similar to that in which lead leg 106 was received by connector block 86 (FIG. 2). Two sense electrodes 180 and 182 are disposed on plug 176 at proximal and distal positions, respectively, and a third sense electrode 183 may be disposed on connector block 174 in the manner described above. In addition, a separator 184 is coupled to plug 176 proximate electrode 182. Separator 184 is similar to separators 128, 129, and 131 described above in conjunction with FIG. 3, and may or may not be physically attached to canister 172. Separator 184 comprises a body 186 and an arm 188 that extends from body 186 to contact canister 172. Body 186 may have a generally annular shape, and may clip onto plug 176 or instead be threaded over the distal end of plug 176 as previously described. Separator 186 functions to maintain the spatial position of sense electrode 182 and, to some degree, sense electrode 180 relative to one another and canister 172. Furthermore, separator 186 prevents sense electrode 182 from contacting canister 172.

Figure 5:
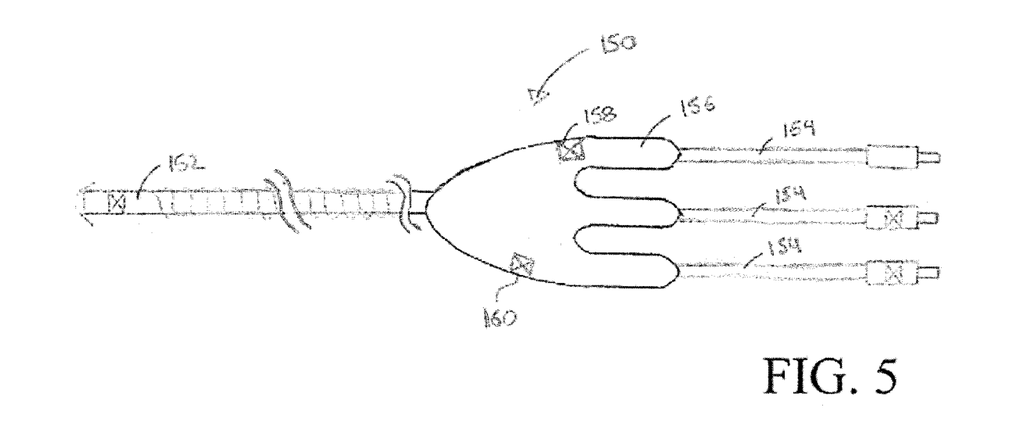
FIG. 5 is an isometric view of a lead assembly suitable for use with a subcutaneous ICD in accordance with a third embodiment of the present invention.
Figure 7:
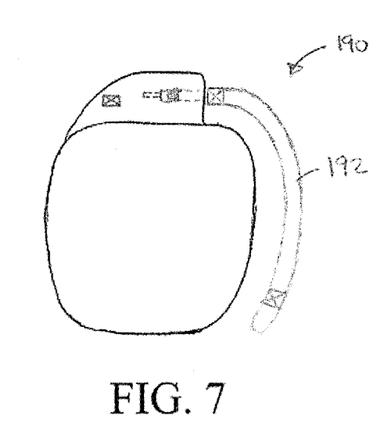
FIGS. 7, 8, and 9 are isometric views of implantable medical devices having rigid plugs in accordance with fifth, sixth, and seventh embodiments of the present invention, respectively.
Figure 8:
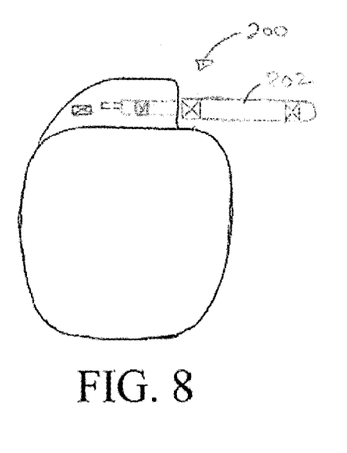
Figure 9:
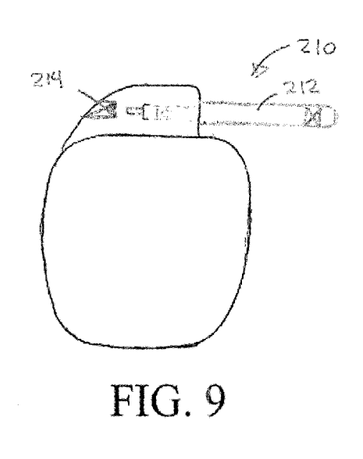

Though plug 176 of IMD 170 was described above as being generally flexible, it should be appreciated that the inventive medical device may employ one or more generally rigid plugs. FIGS. 7, 8, and 9 illustrate three medical devices (i.e., devices 190, 200, and 210, respectively) each having a rigid plug (i.e., plugs 192, 202, and 212) extending therefrom. The plug in each of these embodiments is capable of retaining its shape before, during, and after implantation and may comprise a plug body of hard plastic (e.g., polyurethane with a hardness of 75, which may also be used to form connector block 174) and a rigid metal core. As shown in FIG. 7, the rigid plug maybe pre-bent to generally conform to the contour of the device's canister. Alternatively, the rigid plug may comprise a substantially straight and truncated body (FIGS. 8 and 9). A first sense electrode is distally disposed on the rigid plug, and a second sense electrode may be proximally disposed thereon (FIGS. 7 and 8). In addition, one or more sense electrodes may be disposed on a lead assembly similar to lead assemblies 88 (FIG. 3), 136 (FIG. 4), or 150 (FIG. 5). Lastly, one or more sense electrodes may be disposed elsewhere on the medical device; e.g., on the connector block as shown in FIG. 9 at 214. By employing a rigid plug having one or more sense electrodes disposed thereon, devices 190, 200, and 210 are each configured to maintain the spatial orientation of the sense electrodes relative to each other and relative the device's canister without the use of additional support structures. As stated above, by maintaining the spatial orientation of the sense electrodes in this way, precise and reliable sensing of cardiac activity may be achieved thereby enabling the quick and accurate identification of cardiac arrhythmias. Such a configuration may also be used in conjunction with other implantable devices including, but not limited to, implantable cardioverter defibrillators (e.g., ICD 82) and implantable pulse generators having subcutaneous, epicardial, or endocardial lead systems.

In view of the above, it should be appreciated that an implantable medical device (e.g., an ICD) has been provided wherein the relative positioning of the sense electrodes is maintained, and may be duplicated if desired. Although the invention has been described with reference to a specific embodiment in the foregoing specification, it should be appreciated that various modifications and changes can be made without departing from the scope of the invention as set forth in the appended claims. Accordingly, the specification and figures should be regarded as illustrative rather than restrictive, and all such modifications are intended to be included within the scope of the present invention.

The invention claimed is:

1. An implantable medical device for sensing cardiac activity within a patient's body, comprising:
    a conductive canister;
    control circuitry disposed within said canister;
    a lead assembly extending from said canister;
    at least one sense electrode coupled to said circuitry and disposed on said lead assembly for sensing cardiac activity; and
    at least one spacer coupled between said lead assembly and said canister, maintaining a minimum predetermined distance between said at least one sense electrode and said canister and preventing the sense electrode electrode from contacting said canister.

2. An implantable medical device according to claim 1 wherein said lead assembly comprises:
    a plurality of leads each coupled to said canister;
    a lead body; and
    a furcation for coupling said plurality of leads to said lead body.

3. An implantable medical device according to claim 2 wherein said at least one sense electrode is disposed on said furcation.

4. An implantable medical device according to claim 2 wherein said at least one sense electrode is disposed on at least one of said plurality of leads.

5. An implantable medical device according to claim 4 wherein said at least one spacer is coupled between said canister and said first of said plurality of leads.

6. An implantable medical device according to claim 5 wherein said at least one spacer comprises a shroud coupled to said canister and to said first of said plurality of leads.

7. An implantable medical device according to claim 5 wherein said at least one sense electrode comprises a first electrode and a second electrode each disposed on said first of said plurality of leads, and wherein said at least one spacer comprises a first separator and a second separator coupled to said first of said plurality of leads, said first separator coupled proximate said first electrode and said second separator coupled proximate said second electrode.

8. An implantable medical device according to claim 1 wherein said at least one spacer is coupled to said lead assembly proximate said at least one sense electrode.

9. An implantable medical device according to claim 8 wherein said at least one spacer comprises first and second spacers coupled to said lead assembly, said at least one sense electrode disposed between said first and second spacers.

10. An implantable medical device according to claim 9 wherein said lead assembly comprises a flexible plug, and wherein said at least one sense electrode is disposed on a distal portion of said flexible plug.

11. An implantable medical device according to claim 1 further comprising a connector block coupled between said canister and said lead assembly, and wherein said at least one sense electrode comprises a first electrode and a second electrode, said first electrode disposed on said connector and said second electrode disposed on said lead assembly.

12. An implantable medical device for sensing cardiac activity within a patient's body, comprising:
    a conductive canister;
    control circuitry for monitoring cardiac activity, disposed within said canister;
    a lead assembly extending from said canister;

at least one sense electrode coupled to said control circuitry and disposed on said lead assembly for sensing cardiac activity; and at least one insulative spacer coupled between said lead assembly and said canister, maintaining a minimum predetermined distance and preventing contact between said at least one sense electrode and said canister.

13. An implantable medical device according to claim 12 wherein said lead assembly comprises:

a plurality of leads each coupled to said canister;

a lead body; and a furcation for coupling said plurality of leads to said lead body.

14. An implantable medical device according to claim 13 wherein said at least one sense electrode is disposed on said furcation.

15. An implantable medical device according to claim 13 wherein said at least one sense electrode is disposed on at least one of said plurality of leads.

16. An implantable medical device according to claim 13 wherein said at least one spacer is coupled between said canister and said first of said plurality of leads.

17. An implantable medical device according to claim 12 wherein said at least one spacer is coupled to said lead assembly proximate said at least one sense electrode.

18. An implantable medical device according to claim 17 wherein said at least one spacer comprises first and second spacers coupled to said lead assembly, said at least one sense electrode disposed between said first and second spacers.

19. An implantable medical device according to claim 12 wherein said lead assembly comprises a flexible plug, and wherein said at least one sense electrode is disposed on a distal portion of said flexible plug.

20. An implantable medical device according to claim 12 further comprising a connector block coupled between said canister and said lead assembly, and wherein said at least one sense electrode comprises a first electrode and a second electrode, said first electrode disposed on said connector and said second electrode disposed on said lead assembly.

* * * * *